United States Patent [19]
Gautsch

[11] Patent Number: 6,162,602
[45] Date of Patent: Dec. 19, 2000

[54] AUTOMATIC DIRECT SEQUENCING OF BASES IN NUCLEIC ACID CHAIN ELONGATION

[76] Inventor: James W. Gautsch, 451 S. Granados Ave., Solana Beach, Calif. 92075

[21] Appl. No.: 09/116,617

[22] Filed: Jul. 16, 1998

[51] Int. Cl.[7] .............................. C12Q 1/68; C12P 19/34; C07H 21/04
[52] U.S. Cl. .............................. 435/6; 435/91.1; 536/24.3
[58] Field of Search ....................... 435/6, 91.1; 536/24.3

[56] References Cited

U.S. PATENT DOCUMENTS

| | | | |
|---|---|---|---|
| 4,863,849 | 9/1989 | Melamede | 435/6 |
| 5,552,278 | 9/1996 | Brenner | 435/6 |

OTHER PUBLICATIONS

Milofsky et a. "Native fluorescence detection of Nucleic Acids and DNA restriction fragments in capillary electrophoresis" Analytical Chemistry vol. 65, pp. 153–157, 1993.

Maniatis et al. "Molecular cloning: a laboratory manual" Cold Spring Harbor Laboratory, USA, 1992.

Skoog et al. "Fundamentals of Analytical Chemistry" W.B. Saunders Company, USA, 1988.

*Primary Examiner*—John S. Brusca
*Assistant Examiner*—Jeffrey S. Lundgren
*Attorney, Agent, or Firm*—Fuess & Davidenas

[57] ABSTRACT

An improved apparatus and method for nucleic acid base sequencing by annealing a primer to a nucleic acid template, extending the primer and direct step-wise detecting of incorporated bases, without the use of nucleic acid fragments, extrinsic labeling or electrophoresis, the apparatus described by employing a simple rotary valve system to generate sequential growth of a molecular chain, a laser beam and detection system for determining the amount of native fluorescence quenched in an aliquot of reaction mixture solution as each nucleotide species is extracted from a reactant solution and incorporated into the growing chain.

19 Claims, 4 Drawing Sheets

Detail A

AUTOMATIC DIRECT SEQUENCING OF BASES IN NUCLEIC ACID CHAIN ELONGATION

BACKGROUND OF THE INVENTION

1. Field of the Invention

The present invention generally concerns the sequencing of bases in nucleic acid molecules by repeated separate polymerasecathylzed covalent phosphodiester covalent linkage of each of four deoxyribonucleotide triphosphate to template DNA. The present invention particularly concerns an improved method and apparatus for nucleic acid base sequencing by annealing a primer to a nucleic acid template, extension of the primer and direct step-wise detection of added bases, without the use of nucleic acid fragments, extrinsic labeling or electrophoresis.

2. Description of the Prior Art

Nucleic Acids

Genetic information for living organisms is encoded in deoxyribonucleic acid (DNA) predominately, and in ribonucleic acid (RNA) secondarily. Both, DNA and RNA comprise four building blocks, called nucleotides, chemically bonded in specific sequence to one another to form long polymeric chains containing code sequences for formation of structural genes.

A nucleotide is a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose it is referred to as a nucleotide.

In living organisms, the amino acid residue sequence of a protein or polypeptide is directly related via the genetic code to the deoxyribonucleic acid (DNA) sequence of the structural gene that codes for the protein. Thus, a structural gene can be defined in terms of the amino acid residue sequence, i.e., protein or polypeptide, for which it codes.

An important and well known feature of the genetic code is its redundancy. That is, for most of the amino acids used to make proteins, more than one coding nucleotide triplet (codon) can code for or designate a particular amino acid residue. Therefore, a number of different nucleotide sequences may code for a particular amino acid residue sequence. Such nucleotide sequences are considered functionally equivalent since they can result in the production of the same amino acid residue sequence in all organisms. Occasionally, a methylated variant of a purine or pyrimidine may be incorporated into a given nucleotide sequence. However, such methylations do not affect the coding relationship in any way.

DNA segments that encode certain proteins can easily be synthesized by chemical techniques, for example, the phosphotriester method of Matteucci et al., *J. Am. Chem. Soc.*, 103:3185 (1981). Of course, by chemically synthesizing the coding sequence, any desired modifications can be made simply by substituting the appropriate bases for those encoding the native amino acid residue sequence. However, DNA molecules including sequences exactly homologous to those in desired functional genes are preferred.

Furthermore, DNA segments consisting essentially of structural genes encoding these proteins can be obtained from recombinant DNA molecules containing those genes.

A DNA segment that includes a DNA sequence can be prepared by operatively linking (ligating) appropriate restriction fragments from plasmids using well known methods. The DNA molecules produced in this manner typically have cohesive termini, i.e., "overhanging" single-stranded portions that extend beyond the double-stranded portion of the molecule. The presence of cohesive termini on the DNA molecules is preferred.

Also contemplated by the present invention are ribonucleic acid (RNA) equivalents of the above described DNA segments.

Seguencing Methods

In order to be able to understand and manipulate genes for advantageous medical purposes, it is absolutely essential to be able to determine the precise sequences of said genes. Higher organisms, such as mouse and man, are believed to have haploid genomes containing about 3 billion base pairs. A human genome, with 23 pairs of chromosomes comprising about 100,000 genes, each having an average of 30,000 base pairs, has about 3.3 billion base pairs in total.

Using inheritance patterns of genetic "markers" it has been estimated that there is an abnormal gene in every one or two million base pairs. Cloning the DNA segment involved, allows the testing of the gene's activity, following its inheritance patterns, and diagnosing and treating potential victims of a disease.

Mapping of the complete human genome is a project until relatively recently uncontemplated because of its immensity. However, it has become the largest and potentially the most important project hitherto contemplated.

Although major advances in speeding up the sequencing of these macromolecules have been made, the methods used are cumbersome, labor-intensive and difficult to automate. Two methods have been employed since the early 1970's. The one most commonly used is the enzymatic method developed by Sanger, et al. The other, developed by Maxam and Gilbert, employs chemical degradation. Although both of these techniques are based on the same principles, utilizing gel electrophoresis, the methods of generating the fragments differ. The Sanger dideoxynucleotide method is more amenable to automation because it employs less extreme conditions than the Maxam and Gilbert chemical degradation method.

Generally, as practiced currently, nucleic acid sequencing comprises the following steps:

preparing a template;

generating a series of labeled fragments beginning at a defined point and terminating randomly at points where one of the bases occurs in the sequence;

separating the fragments generated according to size;

detecting the separated fragments; and interpreting the information derived from the separation patterns so obtained.

Preparing a Template

The Sanger dideoxynucleotide sequencing method involves annealing a primer (short piece of synthetic DNA) to a DNA template, and the synthesis of new DNA by the linear addition of deoxynucleosides in a reaction mixture containing a DNA polymerase, other necessary components, and conditions necessary for the reaction to occur.

Generating a Series of Labeled Fragments

Subsequent addition of proper amounts of dideoxynucleotides causes termination of the chain extension at random;

controlled, in part, however, by the concentration of the deoxynucleotide and dideoxynucleotide forms. A separate terminating reaction for each of the four bases is performed, resulting in the generation of randomly terminated fragments. The four groups of fragments represent the complementary sequence information of the template. Fragments so formed are labeled either with radioisotopes, fluorescent dyes or enzymatic reactions. This can be done by incorporating labelled nucleotides, or tagging after formation.

Separating the Fragments

The fragments are separated by slab gel electrophoresis, or the improved capillary gel electrophoresis methods employing agarose or polyacrylamide gels. In either method, the fragments in each of the four sets are loaded in adjacent lanes of a slab gel, or capillary tube, and separated by electrophoresis.

Detecting the Separated Fragments

In slab gels, the separate fragments labeled with radioisotope or chemiluminescent signals are detected by imaging on X-ray film, use of a charge-coupled device (CCD) camera, or by position of fluorescent or enzyme substrate degradation product bands in the gel, as determined by fluorometric, calorimetric or densitometric methods. From capillary columns, the effluent is monitored for the relative band position.

Nucleotides and DNA fragments display native fluorescence (Milofsky, R. E. and E. S. Yeung, Anal. Chem. 1993, 65 153–157), but because of the quenching effect and sometimes intense autoflourescence of the gels, detection of native fluorescence has been effectively employed only under harsh, acidic or basic conditions.

A solid phase DNA mini-sequencing method, employing enzymatic luminometric pyrophosphate detection and obviating the need for electrophoresis, has been described by Nyren, P., et al. Anal. Biochem. 1993, 208, 171–175.

Mass Spectrometry has been applied to DNA sequencing in U.S. Pat. No. 5,453,247; however, this method is not capable of being understood or utilized competently by a large number of artisans in the field.

A new, and potentially useful method of detection by means of an electronic chip is employed in certain circumstances in detecting single base differences in target molecules.

Interpreting the Information

As is known to the practitioners in the field, interpretation of the electrophoresed fragment data is both laborious and time consuming.

A direct sequencing method, lending itself to automation, was described in U.S. Pat. No. 4,863,849 issued to Robert Melamede in 1989. This method eliminates much of the labor-intensive and interpretation difficulties associated with the currently used sequencing methods. The method patent also partially describes an apparatus useful for automating the method. There are significant difficulties with the apparatus described. One, is the fact that a single reaction chamber is used. This does not permit running a parallel control, or a plurality of samples, thus, requiring laborious methods of recognizing and correcting "mistakes." Two, a multi-chambered apparatus greatly facilitates the speed of sequencing in cases where a multiplicity of fragments needs to be sequenced. Additionally, in large laboratories and preparation facilities, a multi-chambered apparatus permits sequencing of many diverse molecules.

Accordingly, it would be highly desirable to eliminate many of these cumbersome procedures in performing the sequencing in the conventional laboratory setting, performed by anyone with basic knowledge of laboratory procedures, and permitting the rapid processing of a multiplicity of samples.

SUMMARY OF THE INVENTION

The present invention eliminates all but the first step in the complex procedure of sequencing nucleic acids, and involves only a direct method of determining base sequence.

As its first object, the present invention contemplates an apparatus for sequencing bases in deoxyribonucleic acid, DNA, or, equivalently, ribonucleic acid, RNA, having a valve/chamber assembly for carrying out steps in the is sequencing process. The assembly has a movable subassembly having a plurality of separate reservoirs, each designated for holding a one of an admixture and a buffer, It also has a static subassembly containing at least one reaction chamber with an immovable primer attached. There is a first fluid flow coupler for first sequentially flow communicating the admixture from a one of the moveable subassembly's plurality of reservoirs downstream to the static subassembly's reaction chamber to produce (i) an elongating molecular chain grown on the primer and (ii) unreacted components, and for second flow communicating the buffer from another one of the moveable subassembly's plurality of reservoirs downstream to the static subassembly's reaction chamber to flush the reaction chamber to produce a wash solution.

There is also a second fluid flow coupler for sequentially flow communicating the unreacted components from the static subassembly's reaction chamber and means for moving the moveable subassembly relative to the static subassembly and for transporting fluid through the valve/chamber assembly in order that it may be sequentially reacted. There is also means for detecting the presence of nucleotides in a post-reaction solution received from the reaction chamber via the second fluid flow coupler.

The movable subassembly is a rotor; wherein the static subassembly is a stator; and the means for moving is rotating the rotor relative to the stator. The number of reservoirs in the rotor is can be 8 or more. The odd numbered of the eight reservoirs, 1, 3, 5, 7, in the rotor contain a reaction admixture with polymerase, and even numbered reservoirs 2, 4, 6, 8 in the rotor contain a buffered wash solution. The rotor has an outlet port and the stator has both an inlet and an outlet port. The outlet port of the rotor is juxtaposed to the inlet port of the stator for the ingress of admixture or of buffer into the reaction chamber. The unreacted components and the wash solution exit the stator through the stator's outlet port. Egress of reaction mixture from the rotor's reservoirs to the stators reaction chamber is controlled by sequential rotational alignment of juxtaposed apertures.

The means for detecting referred to above includes an excitation beam generating means for producing an excitation beam that induces native fluorescence emission in target molecules, which is determined by a means for measuring fluorescence emitted, and the result is recorded by a recording data means, and an elongating nucleic acid chain is plotted by a means for sequentially plotting detected nucleotides.

The apparatus may also possess a flow injection means incorporated upstream from the detecting means to adjust the pH of the post-reaction effluent and thereby increase sensitivity of detection, and a quartz flow-through cell, facilitating passage of the excitation beam and the fluorescence emitted.

The detection may include excitation of by an eximer laser beam, which would be measured by means having one or more condenser lenses for condensing fluorescent light emitted from the excited sample molecules; one or more interference filters for selecting an appropriate wavelength of the fluorescence light emitted; a photomultiplier for detecting and enhancing fluorescence photons emitted; and a means for converting detected photons to signals suitable for computer analysis. A computer, a plotter and computer software suitable for analyzing the signals in respect of the detected fluorescence photons is also incorporated in the detection.

Means for rotating the rotor subassembly about the stator subassembly may be a controllable stepper motor, controlled by a computer. The means for transporting fluid through the entire valve/chamber assembly may be a pump that is integral with the valve/chamber assembly, and which moves fluid by peristaltic action.

A second object contemplated by the invention is a kit for sequencing bases in deoxyribonucleic acid, DNA, or, equivalently, ribonucleic acid, RNA. The base sequencing kit comprises four separate vessels, each containing a sufficient amount of an appropriate reaction admixture comprising, in the case of DNA template, one of four different individual deoxyribonucleotide triphosphate, dNTP, substrates or, equivalently in the case of template RNA, four different ribonucleotide triphosphate, NTP, substrates, each substrate at an associated given concentration $N_i$, plus polymerase. Each reaction mixture admixture is capable of facilitating catalyzed covalent linkage of the associated one of the four individual dNTP, or, equivalently, NTP, to the template DNA or, equivalently, RNA.

The kit also has a vessel containing insoluble solid medium for attachment is of a DNA (or RNA) primer:template, and a vessel of a wash solution buffered identically to the reaction admixture. All kit components must be provided in sufficient amounts to perform at least one sequencing procedure on a molecule of an average length.

A third object of the invention is an improved method for sequencing bases in deoxyribonucleic acid, DNA, or, equivalently, ribonucleic acid, RNA, without the use of radioisotope, fluorescent dye or any extrinsic label. The base sequencing method of this invention comprises reacting in each of four separate vessels (i) a template DNA, or, equivalently, RNA, plus (ii) in the case of template DNA, four different individual deoxyribonucleotide triphosphate, dNTP, substrates or, equivalently in the case of template RNA, four different ribonucleotide triphosphate, NTP, substrates, each substrate at an associated given concentration $N_i$, plus (iii) a suitable primer oligonucleotide annealed to the template DNA, or, equivalently, the template RNA, plus (iv) a polymerase.

Each reaction transpires by repeated separate polymerase-cecathylzed covalent phosphodiester polymerized catalyzed covalent linkage of the associated one of the four individual dNTP, or, equivalently, NTP, to the template DNA or, equivalently, RNA.

After completion of the reactions, the single reaction vessel in which an associated final concentration, $N_f$, of dNTP or, equivalently, NTP, has decreased, $N_f/N_i<1$ is determined as an indication of the single, free nucleotide that has reacted. Thus, as a corresponding indication of the base at the present position on the template DNA, or, equivalently, the template RNA is determined. The method of sequencing bases in nucleic acid, after the determining, further comprises: recording the base indicated at the present position on the template DNA, or, equivalently, the template RNA; adding the indicated base to the primer that is annealed to the template DNA, or, equivalently, the template RNA; and repeating the reacting, the determining, the recording and the adding until the entire template DNA, or, equivalently, the template RNA, is sequenced.

The essence of this method is that the elongating chain must be immobilized; that the single nucleotides and polymerase be free to react and in no way restricted; and that there is no dilution of the spent effluent These and other aspects and attributes of the present invention will become increasingly clear upon reference to the following drawings and accompanying specification.

Detail A depicts the juxtaposed apertures of the concentric chamber/vessel bodies, forming an opening for solution to pass through from a vessel to a reaction chamber.

Figure 3:
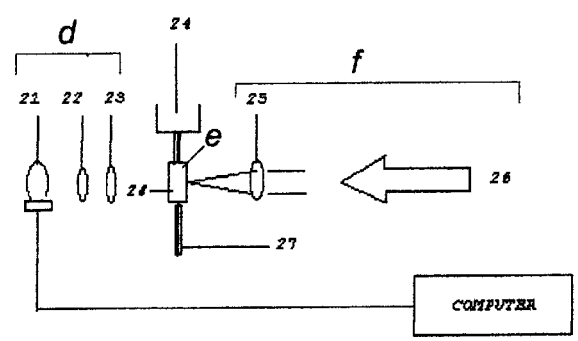

FIG. 3 depicts schematically a detecting and measuring device, comprising the path of an excitation beam and the various lenses and filters useful for focusing the beam, capturing emitted wavelength, and converting the signals captured into a medium suitable for computer analysis of data.

Figure 1:
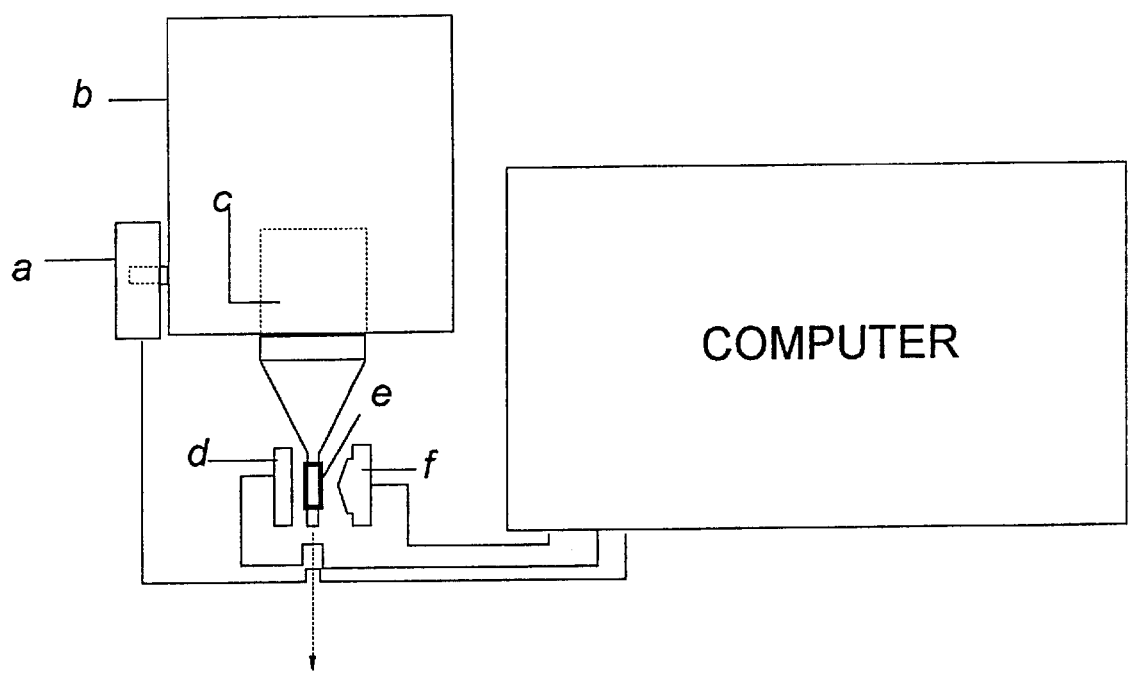
FIG. 1 depicts a diagrammatic side view of the entire DNA sequencing system which is the object of this invention.
Figure 2:
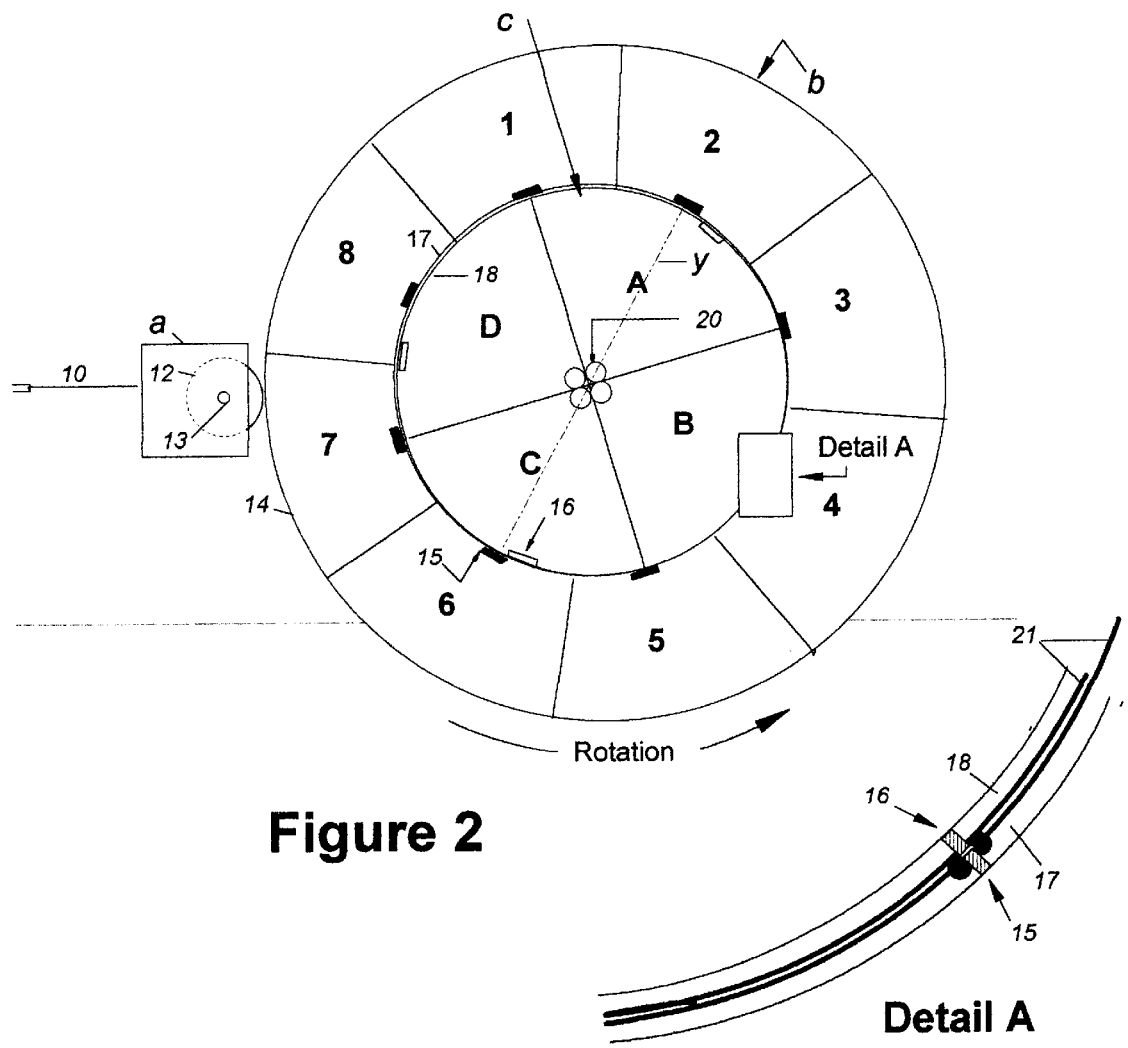
FIG. 2 is a cross-sectional top plan view, at X of FIG. 2, of the sequencing rotary valve/chamber apparatus, showing the centrally located reaction chambers surrounded by an array of vessels laterally disposed and containing, alternately, a reaction admixture and a wash solution.
Figure 4:
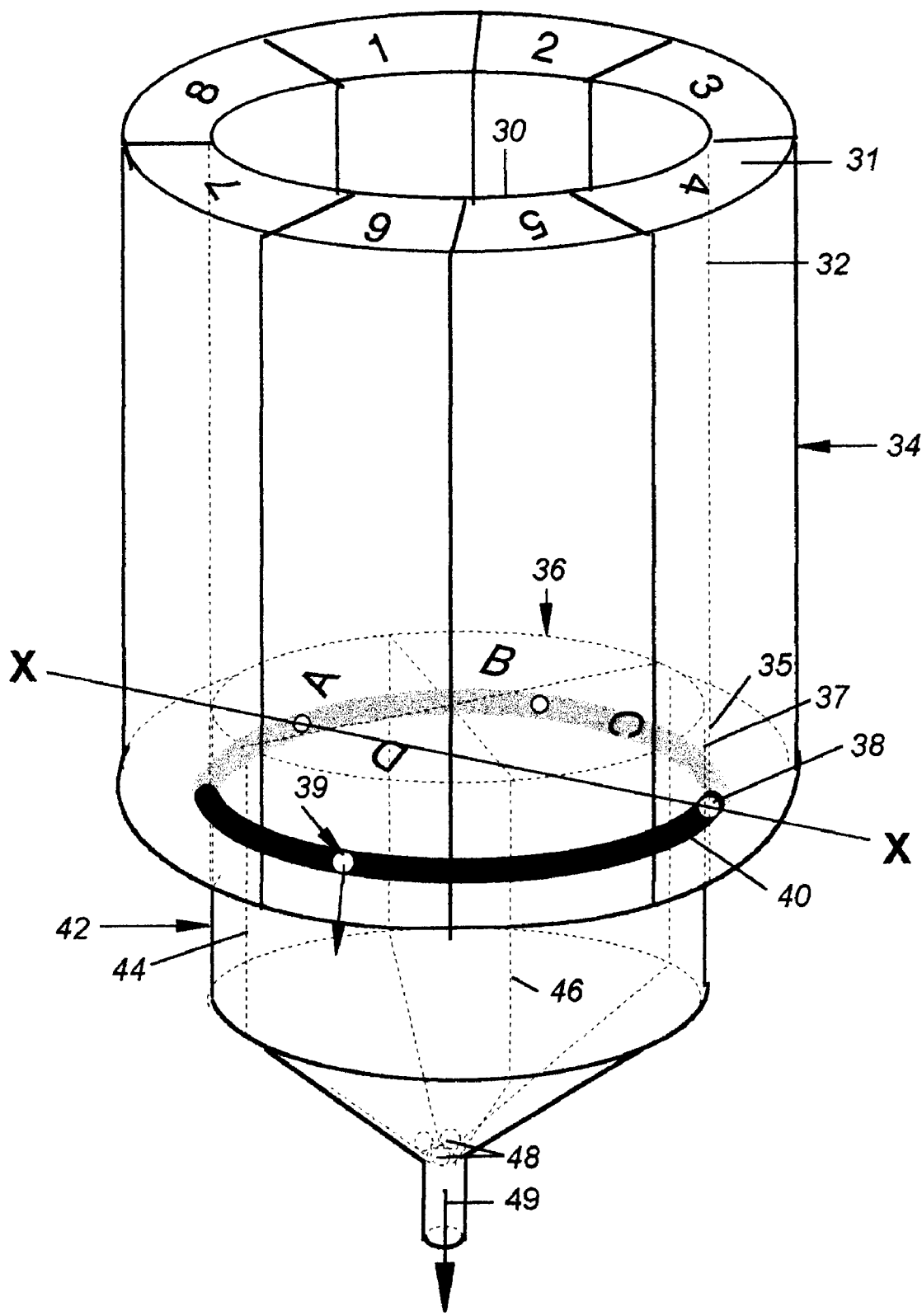

FIG. 4 is a diagrammatic perspective view of the rotary valve body of the preferred embodiment of a nucleic acid sequencing apparatus in accordance with the present invention previously seen in FIGS. 1 and 2.

Figure 5:
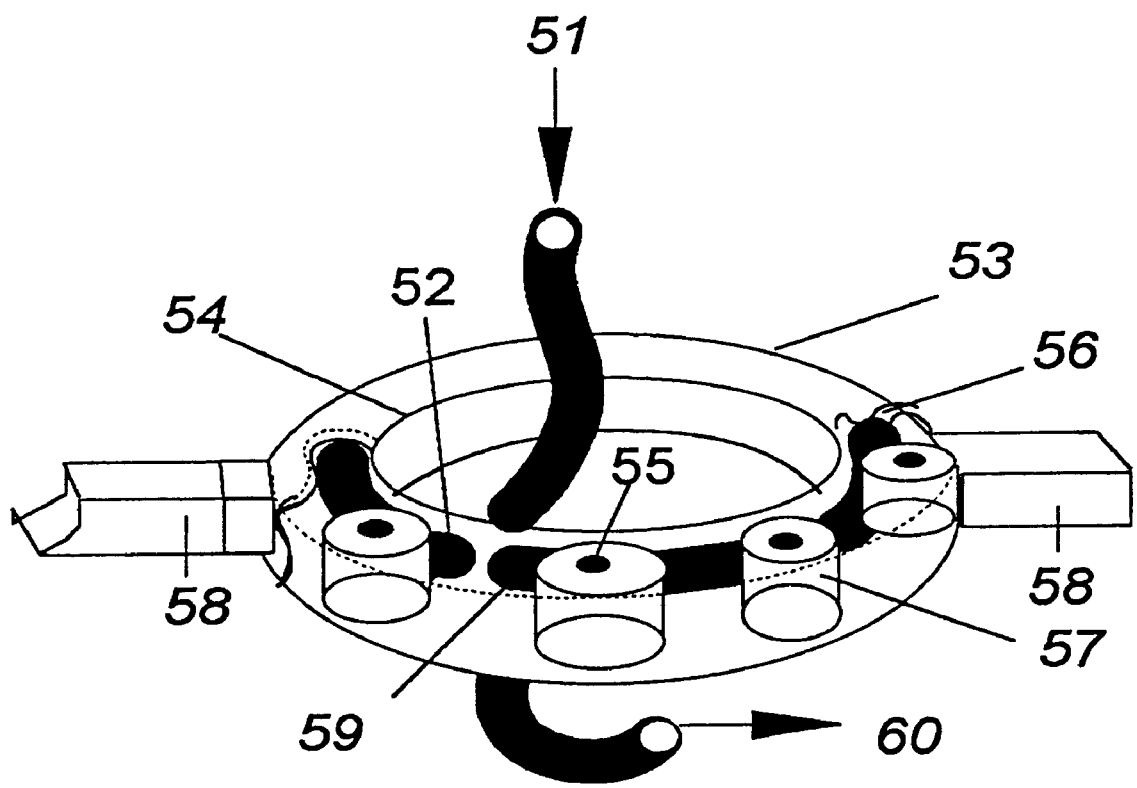

FIG. 5 shows, in cut-away perspective view, the pump located downstream from the reaction chamber.

DESCRIPTION OF THE PREFERRED EMBODIMENTS

Example 1

Apparatus For Automatic Direct Sequencing

In one preferred embodiment, an improved apparatus for sequencing nucleic acid molecules is a simple rotary valve/chamber system assembly, as seen in FIG. 1, comprised of a stator subassembly c, a rotor subassembly b, a stepper motor a, and a detection means d, e, f, acting in conjunction. Although a rotary system is described herein, a linear, sliding system would also be contemplated as an alternative.

FIG. 2 (taken at X—X of FIG. 4) shows diagrammatically, in top plan view, the rotor subassembly b having a first container with a plurality of separate reservoir vessel chambers in an annular array 1–8. The donut-shaped container is formed from two hollow, coaxial cylindrical bodies, the smaller 17 within and coaxially aligned with the larger 14, forming the inner and outer walls of the chamber array. The space formed between the cylindrical bodies is closed at the bottom. Thus, an annular container with a large central bore (shaded) is formed. Eight or more sequentially numbered vessels 1–8 in an annular array are radially disposed between the two cylinder walls, and juxtaposed to each other. The inner and outer walls of the reservoir chambers are formed by the walls of the inner 17 and outer 14 cylindrical walls, and the sidewalls are formed by equally spaced partitions of the container. The bottom of each of the chambers so formed is closed, but for an inward facing aperture FIG. 4, 15, and the top of each chamber may have a lid. The number of chambers is not restricted to eight, but can be any number, as required.

The alternating, odd numbered chambers 1, 3, 5, 7 in the array each contain a reaction admixture hereinabove described, having one of the four nucleotides. The even numbered chambers 2, 4, 6, 8 contain a buffered wash solution. The resultant rotatable chamber subassembly b forms the rotor portion of the combined stator/rotor assembly.

Positioned downstream, internal and coaxial to the rotor subassembly is the close-fitting stator subassembly c, containing the reaction chambers A, B, C, D. The stator subassembly is comprised of a hollow cylindrical body 18 coaxial, internal and downstream to the rotor subassembly b. The cylinder 18 is closed with a lid at the top 19 and tapered to the bottom, the bottom wall forming a cone-like funnel. The cylindrical void thus formed within is partitioned 44, 46 into one or more radially disposed reaction chambers A-D that are intended herein to contain a nucleic acid template:primer attached to a solid substrate for the chain elongation reaction.

As easily seen in FIGS. 2 and 3, in the instant embodiment, the number of reaction chambers is four A–D. The cone-like bottom of the chamber has one or more (4 in this case) centrally arranged metering nozzles 20, one for emptying each chamber.

The stator subassembly c has a peripheral, annular support bushing and seal means 21 (Detail A), which may contain roller bearing surfaces, or be formed from low-friction materials such as Teflon, disposed about its elongated, cylindrical body in the form of a band, said bushing forming a resilient annular sealing barrier between the two subassemblies b and c. This annular barrier contains an annular groove and an annular seating surface, which form the stationary inner annular race. Within this race, is contained a latitudinal array of inlet apertures 16, circumferentially disposed and appropriately spaced.

The rotor subassembly has an opposing inner resilient annular bushing means 21, having a fluid-tight seal means rotatably associated in relation to the stator bushing means. The rotor subassembly is positioned so that it rotatably circumscribes, and aligns with, the stator subassembly, so that the apertures of both subassemblies are on an identical horizontal plane.

Reservoir chamber outlet apertures may have annular alignment embossments to decrease the amount of sliding friction within the bushing and seal means Detail A, and to help wipe the race clean.

Reaction chamber inlet apertures are radially disposed in such a precisely offset manner that only one opening is in alignment with a rotor assembly outlet aperture at any one time point permitting reaction admixture fluid, or wash fluid, to enter into one reaction chamber only, for example, in this case, wash solution from vessel 4 into chamber B. Detail A shows such an alignment. It can be seen in FIG. 2 that vessel 2 has already been in contact with chamber A, and vessel 6 is next to connect with chamber C, followed by vessel 8 connecting with chamber D. Then, vessel 3 will connect with A, 5 with B, 7 with C, and 1 with D, respectively.

Means for rotating the vessel-containing rotor subassembly b about the centrally located stator subassembly c, containing the reaction chamber array, comprises a step motor a regulated by computer stepper software programmed to synchronize with effluent detection at d, e, f, (FIGS. 1, 2, 5) and recording means as described hereinbelow. Although an external mechanism , with a drive wheel is described, any other drive mechanism, either internal or external is contemplated.

With each step in rotational sequence, one aperture means for egress of admixture from its upstream vessel, and one aperture means for ingress into the downstream reaction chamber are juxtaposed, allowing downstream passage of the admixture solution into the reaction chamber. The egress and ingress is controlled by the above described simple rotary valve system. As the two concentric subassemblies rotate in relation to each other, their respective aperture means slide by each other to progressively open the connecting apertures. The step motor stops at full opening to allow the admixture, or wash solution, to enter the chamber containing an immobilized DNA template chain that is undergoing elongation. When the reaction chamber is properly filled, the motor is activated again, and the sliding action closes the apertures. The reaction time is regulated by the software, but is nearly instantaneous. When the apertures are again aligned by the sliding action, the admixture solution containing unreacted nucleotides empties through the bottom metered nozzle and the chamber is refilled with the wash solution. This process repeats continuously until the bases in the entire elongated strand are recorded in sequence.

The hereinbefore described apparatus may be placed in an incubator to control the temperature of the reaction, or it may have a built-in temperature control chamber surrounding the rotor assembly.

Referring now to FIG. 3, below the stator subassembly is a collecting vessel 24, which receives effluent from a reaction chamber. As the reaction is admixture effluent, containing unreacted nucleotides, leaves the reaction chamber, it is routed through a quartz detection cell e, wherein it is subjected to an excitation beam f. Where an adjustment of pH values of the molecules in solution is required for optimal visualization of the native fluorescence, such adjustment can be made by the flow injection method described by Milofsky and Yeung (supra).

The excitation beam producing means 26 can be any appropriate wavelength emitter, such as a KrF or argon ion laser, a UV beam, or the like. In the above described preferred embodiment, the excitation beam is produced by an eximer laser beam generating means, such as a KrF eximer laser, e.g. Potomac Photonics Model GX-1000 waveguide laser, generating a laser light beam that is focused on and excites the target nucleotide molecules in solution, thereby causing a strong beam of emitted autofluorescence.

The presence and amount of nucleotide in solution is measured by one of several suitable optical measuring devices d, such as a fluorescence sensor, or a direct UV sensor, and the like. In this example of a preferred embodiment, the fluorescence measuring device is apertured for passage of the autofluorescence beam, and includes one or more condenser lenses 22 for condensing fluorescent light emitted from the excited sample; one or more interference filters 23 for selecting the appropriate fluorescence wavelength; a photomultiplier 21 for detecting the fluorescence emitted; and means for converting photons detected into media suitable for computer analysis, for example, converting algorithmic signals to digital CCD.

The data recording means includes a computer, recorder and plotter, and suitable software. The raw data is fed into the computer automatically, wherein each event, synchronized with the valve assembly, is recorded, analyzed and the resulting analysis is documented as an elongating DNA molecule.

Interposed in between the reaction chamber and the detection device, is a peristaltic pump as shown in FIG. 5, a cut-away perspective view. The rotating portion 53 of the pump, comprising pressure rollers 57 is attached to the bottom of the elongated cylinder of the rotor subassembly at 68 (see FIG. 4 also). The pressure rollers pivot on miniature shafts 55. The rollers may be composed of Teflon, or may be steel bearing assemblies. The stationary part of the pump 54 is either integral to a cylindrical extension of the stator subassembly at 54 (FIG. 4). The channel transporting the fluid can be any flexible, resilient tubing, such as Tygon and the like. The tubing enters the pump 59, is fixed securely and wound around the static portion 54, and exits at 69. As the fluid enters at 51 from the reaction chamber, the rotating portion of the pump 53, activated by the step motor a, turns about 54, forcing the fluid along the tubing by peristaltic action of the rollers 57, leaving the pump at 60.

The sample template in each reaction chamber is thus processed separately and independently from that in any other reaction chamber, permitting simultaneous analysis of the nucleotide sequences of as many samples of DNA as there are reaction chambers in the stator subassembly.

Example 2

Nucleic Acid Sequencing Kit

A convenient nucleic acid sequencing kit for use with the above described apparatus is described below. Components of this kit are as follows:

A container [A] of oligonucleotide sequencing primer;

A container [B] having solid substrate materials, for example, magnetic beads, thin cellulose membrane, small filter discs, and the like;

A container [C] of stick-down catalyst, or conjugant, and appropriate buffer solution for the reaction;

Four containers [$N_{1-4}$] of nucleotides, reagent grade, each container having a single base, the type dependent on the type of template, in a solution described hereinbefore as admixture;

A container [P] of polymerase enzyme, e.g., sequenase, type dependent on type of template to be sequenced;

A container [W] of wash solution sufficient to carry out an average sequencing operation; and Two containers [X, Y] of buffers to adjust the pH of the effluent for maximum emission of fluorescence.

The entire kit is intended to be packaged in a formed styrofoam container to accommodate all of the above containers. All containers are to be labelled by a specific letter, as well as by specific identification of its contents. An instruction manual outlining the methods and protocol for performing direct sequencing as described herein is to be included.

Example 3

Direct Sequencing Method

Preparation of Nucleic Acid Template

A particular gene or nucleic acid sequence is PCR-cloned to amplify DNA by conventional methods (e.g., see Nyren, P, et al. (1993) *Anal Biochem.* 208, 171–175). The PCR product is immobilized by, for example, covalently coupling streptavidin to Dynabeads 280 magnetic beads (Dynal A S, Norway) used as described by the manufacturer to the 5' end of the DNA fragment. Single-stranded DNA is obtained by incubating in 0.1 M NaOH for 5 minutes. A sequencing primer is annealed (e.g., Primer set A solution of the Template Preparation kit, Dynal A S, Norway) for 5 minutes at 65° C. and the mixture is cooled to room temperature. The template is now ready for sequencing.

The template may be made insoluble by any of a number of other means that are known to the practitioners in this field. For example, the DNA fragment may be attached to thin film, or laid down on a microtitre plate, or a microchip.

Preparation of a Reaction Admixture

An individual reaction admixture comprises (in the case of DNA template) one of four unlabeled dNTPs and a DNA polymerase, for example, Sequenase (U.S. Biochemical, Cleveland, Ohio) in solution in an appropriate buffer system, each nucleotide being in a separate vessel. Thus, vessel 1 contains a reaction admixture mixture comprising dGTP plus polymerase; vessel 2 contains dATP plus polymerase, and so forth.

Direct Sequencing Reaction

An aliquot of the reaction admixture described above, containing a polymerase (e.g. Sequenase ver. 2.0) and a single dNTP in an appropriate concentration to permit detection and quantitation in the post-reaction supernatant is added to an aliquot of immobilized nucleic acid template. The reaction mixture is incubated at room temperature; the reaction supernatant is removed for detection and analysis; and the immobilized elongating chain fragments are washed with a buffered wash solution.

The same procedure is repeated with every one of the four reaction admixture vessels. Aliquots of the reacted supernatant solution are sequentially collected in appropriate vessels, for example, in microtiter plates.

Detection and Analysis

Each aliquot of reacted supernatant is read and analyzed by any one of a number of methods known to a practitioner in the field, for example, by quantitating the emission of native fluorescence caused by irradiating with a laser beam. If quenching of fluorescence is found to be bothersome, salt, or another precipitant, or flocculent, may be added to the vessels to precipitate the polymerase out of the post-reaction supernatant solution, thereby, eliminating its quenching effect. The precipitate is spun down and the presence and relative amount dNTP in the supernatant is determined. A diminution of dNTP in the solution indicates that that particular dNTP was incorporated in the chain-elongation reaction. The diminution of dNTP is quantitated relatively, and determination is made of the incorporation of a single or multiple base at that point in the sequence by comparing the degree of diminution.

Other means of detection are available, for example, the luminometric inorganic phosphate detection assay described by Nyren, et al, supra. It is, however, desirable to maintain detection by a direct method, not involving secondary reactions.

In accordance with the preceding explanation, variations and adaptations of the base sequencing apparatus of the present invention will suggest themselves to a practitioner of the molecular biology arts. In the spirit of this invention, these and other possible variations and adaptations of the present invention, and the scope of the invention, should be determined in accordance with the following claims, only, and not solely in accordance with that embodiment within which the invention has been taught.

What is claimed is:

1. An apparatus for sequencing bases in deoxyribonucleic acid, DNA, or, equivalently, ribonucleic acid, RNA, the base sequencing apparatus comprising:

a valve/chamber assembly for carrying out steps in the sequencing process, comprising;

a movable subassembly having a plurality of separate reservoirs, each designated for holding a one of an admixture and a buffer, a static subassembly containing at least one reaction chamber containing an immovable primer, a first fluid flow coupler for first sequentially flow communicating the admixture from a one of the moveable subassembly's plurality of reservoirs downstream to the static subassembly's reaction chamber to produce (i) an elongating molecular chain grown on the primer and (ii) unreacted components, and for second flow communicating the buffer from another one of the moveable subassembly's plurality of reservoirs downstream to the static subassembly's reaction chamber to flush the reaction chamber produce a wash solution;

a second fluid flow coupler for sequentially flow communicating the unreacted components from the static subassembly's reaction chamber;

means for moving the moveable subassembly relative to the static subassembly;

means for transporting fluid through the valve/chamber assembly in order that it may be sequentially reacted; and means for detecting the presence of nucleotides in a post-reaction solution received from the reaction chamber via the second fluid flow coupler.

2. The apparatus for sequencing bases according to claim 1 wherein the movable subassembly comprises a rotor; wherein the static subassembly comprises a stator; and wherein the means for moving is rotating the rotor relative to the stator.

3. The apparatus for sequencing bases according to claim 2 wherein the number of reservoirs in the rotor is 8.

4. The apparatus for sequencing bases according to claim 3 wherein the odd numbered of the eight reservoirs, 1, 3, 5, 7, in the rotor contain admixture in the form of polymerase, and wherein the even numbered reservoirs 2, 4, 6, 8 in the rotor contain buffer in the form of a buffered wash solution.

5. The apparatus for sequencing bases according to claim 2 wherein the rotor has and defines an outlet port; wherein the stator has and defines both an inlet and an outlet port; and wherein the outlet port of the rotor is juxtaposed to the inlet port of the stator for the ingress of admixture or of buffer into the reaction chamber; and wherein the unreacted components and the wash solution exit the stator through the stator's outlet port.

6. The apparatus for sequencing bases according to claim 5, wherein egress of reaction mixture from the rotor's reservoirs to the stator's reaction chamber is controlled by sequential rotational alignment of juxtaposed apertures.

7. The apparatus for sequencing of bases according to claim 1 wherein the means for detecting includes an excitation beam generating means for producing an excitation beam inducing native fluorescence emission in molecules.

8. The apparatus for sequencing of bases according to claim 7 wherein the means for detecting further includes a means for measuring fluorescence emitted.

9. The apparatus for sequencing bases according to claim 1 wherein recording data means records the measured amount of fluorescence emitted.

10. Apparatus for sequencing bases according to claim 1 further comprising:

means for sequentially plotting detected nucleotides as a plot of an elongating nucleic acid chain.

11. The apparatus for sequencing bases according to claim 1 comprising:

a flow injection means incorporated upstream from the detecting means to adjust a pH of the post-reaction and thereby increase sensitivity of detection.

12. The apparatus for sequencing bases according to claim 8 wherein the means for detecting includes a quartz flow-through cell facilitating passage of the excitation beam and the fluorescence emitted.

13. The apparatus for sequencing bases according to claim 7 wherein the excitation means includes an eximer laser.

14. The apparatus for sequencing bases according to claim 1 wherein the detection means further comprises:

one or more condenser lenses for condensing fluorescent light emitted from the excited sample molecules;

one or more interference filters for selecting an appropriate wavelength of the fluorescence light emitted;

a photomultiplier means for detecting and enhancing fluorescence photons emitted; and a means for converting detected photons to signals suitable for computer analysis.

15. The apparatus for sequencing bases according to claim 14 further including a computer, a plotter and computer software suitable for analyzing the signals in respect of the detected fluorescence photons.

16. The apparatus for sequencing bases according to claim 2 wherein the means for rotating the rotor subassembly about the stator subassembly comprises:

a controllable stepper motor;

a computer for controlling the stepper motor.

17. The apparatus for sequencing bases according to claim 1 wherein the means for transporting fluid through the valve/chamber assembly comprises a pump.

18. The apparatus for sequencing bases according to claim 17 wherein the pump is integral with the valve/chamber assembly.

19. The apparatus for sequencing bases according to claim 18 wherein the integral pump moves fluid by peristaltic action.

* * * * *